(12) United States Patent
Cox

(10) Patent No.: US 12,721,314 B2
(45) Date of Patent: *Sep. 1, 2026

(54) SOUND PROTECTION CAP FOR ANIMALS

(71) Applicant: Pamela Cox, Justiceburg, TX (US)

(72) Inventor: Pamela Cox, Justiceburg, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 19/012,575

(22) Filed: Jan. 7, 2025

(65) Prior Publication Data

US 2025/0143262 A1 May 8, 2025

Related U.S. Application Data

(63) Continuation of application No. 18/260,217, filed as application No. PCT/US2022/038928 on Jul. 29, 2022, now Pat. No. 12,185,694.

(60) Provisional application No. 63/227,667, filed on Jul. 30, 2021.

(51) Int. Cl.
*A01K 13/00* (2006.01)
*A61F 11/14* (2006.01)

(52) U.S. Cl.
CPC ............ *A01K 13/006* (2013.01); *A61F 11/14* (2013.01)

(58) Field of Classification Search
CPC ..... A01K 13/006; A01K 27/002; A61F 11/14; A61F 11/06
See application file for complete search history.

(56) References Cited

U.S. PATENT DOCUMENTS

| | | | |
|---|---|---|---|
| 3,005,203 A | 10/1961 | Aileo | |
| 7,946,256 B2 | 5/2011 | Mann | |
| 11,122,356 B1 | 9/2021 | Braun et al. | |
| 2005/0042437 A1 | 2/2005 | Ramesh et al. | |
| 2007/0062462 A1 | 3/2007 | McGuire | |
| 2010/0307427 A1 | 12/2010 | Mann et al. | |
| 2011/0031059 A1 | 2/2011 | Parish et al. | |
| 2015/0144073 A1* | 5/2015 | Mills | A01K 13/006 119/851 |
| 2015/0342716 A1 | 12/2015 | Haught | |
| 2016/0337745 A1 | 11/2016 | Adams | |
| 2019/0374323 A1 | 12/2019 | Mckay et al. | |
| 2021/0137072 A1 | 5/2021 | Beck et al. | |
| 2021/0378806 A1 | 12/2021 | Haught et al. | |

(Continued)

FOREIGN PATENT DOCUMENTS

| | | |
|---|---|---|
| WO | 2018197571 A1 | 11/2018 |
| WO | 2020091899 A2 | 5/2020 |

*Primary Examiner* — Trinh T Nguyen

(57) ABSTRACT

The disclosure provides a device for protecting the hearing of animals. The device is a sound protection cap constructed of formable material, e.g., a soft acoustical material, and adjustable straps to comfortably fit over the ears and on the head of an animal, such as a dog. The sound protection cap can come in different sizes to insure a good fit regardless the ear type or head shape of the animal. The multiple adjustments and formable material allows the sound protection cap to conform around the ears/head of the animal and stay in place. The sound protection cap can be positioned on an animal to provide hearing protection throughout exposure to loud sounds. In different examples, the sound protection cap includes: (1) an external ear cover (EEC) and (2) a mounting adjuster having a neck adjuster and an ear adjuster coupled to the EEC.

20 Claims, 9 Drawing Sheets

(56) References Cited

U.S. PATENT DOCUMENTS

2023/0008652 A1* 1/2023 Weitzel ................ A01K 13/006
2023/0050947 A1 2/2023 Jordan et al.

* cited by examiner

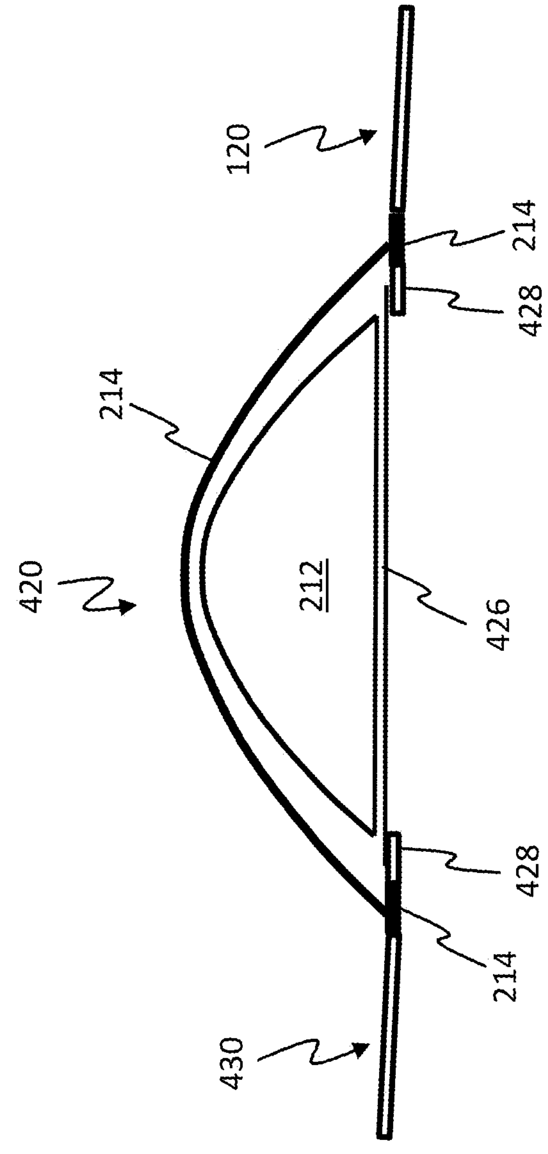
120
214
428
214
420
212
426
428
214
430
FIG. 5
500

SOUND PROTECTION CAP FOR ANIMALS

CROSS-REFERENCE TO RELATED APPLICATION

This application is a continuation application of U.S. application Ser. No. 18/260,217, filed on Jun. 30, 2023, as the National Stage of International Application No. PCT/US2022/038928 filed on Jul. 29, 2022, entitled "A SOUND PROTECTION CAP FOR ANIMALS," which claims the benefit of U.S. Provisional Application Ser. No. 63/227,667, filed by Pamela Cox on Jul. 30, 2021, entitled "A SOUND PROTECTION CAP FOR ANIMALS," commonly assigned with this application and incorporated herein by reference in its entirety.

TECHNICAL FIELD

This application is directed, in general, to hearing protection and, more specifically, to a hearing protective device for animals.

BACKGROUND

Dogs assist people in various jobs, such as, search and rescue, hunting, herding, guiding, and police and military actions. Dogs also make great pets. Whether a service dog, a working dog, or a pet, dogs often end up at locations where they are exposed to noises. This is a concern since dogs, like people, are susceptible to noise-induced hearing loss. For example, owners often take their dogs to concerts, sporting events, fireworks, and on airplanes where they can be exposed to potentially damaging sound. Repeated exposure to such potentially damaging sounds can be especially troublesome since prolonged exposure to loud noises can often have the greatest effect on a dog's hearing loss. Unlike their owners, however, dogs cannot simply put on hearing protection when needed.

SUMMARY

In one aspect, the disclosure provides a sound protection cap for an animal having a neck strap and an ear strap. In one example, the sound protection cap includes: (1) an external ear cover (EEC) and (2) a mounting adjuster having a neck adjuster and an ear adjuster positioned on opposite sides of an apex of the EEC that are adjustable for conforming the EEC around the head and ears of the animal, wherein the neck adjuster is adjustable for positioning the neck strap around the neck and behind the ears of the animal and the ear adjuster is adjustable for positioning the ear strap around the head and in front of the ears.

In another example a sound protection cap for an animal is disclosed that includes: (1) an adjustable neck strap, (2) an adjustable ear strap, (3) a first external ear cover (EEC) and a second EEC that each include a sound reduction layer and a layer of pliable material, wherein the adjustable neck strap and the adjustable ear strap are coupled to the first EEC and the second EEC, and (4) a mounting adjuster having a neck adjuster and an ear adjuster attached to opposite sides of an apex of the first EEC and an apex of the second EEC, wherein the neck adjuster is adjustable for positioning the adjustable neck strap around the neck and behind the ears of an animal and the ear adjuster is adjustable for positioning the adjustable ear strap around the head an in front of the ears.

In yet another example a sound protection cap for an animal is disclosed that includes: (1) a first external ear cover (EEC) and a second EEC that each include at least one sound reduction layer having a shape of a pentagonal prism with a concave portion and (2) a mounting adjuster, removably coupled to the first EEC and the second EEC, wherein the mounting adjuster includes a neck adjuster and an ear adjuster attached to opposite sides of an apex of the first EEC and an apex of the second EEC, wherein the neck adjuster is adjustable for positioning an adjustable neck strap around the neck and behind the ears of the animal and the ear adjuster is adjustable for positioning an adjustable ear strap around the head an in front of the ears.

BRIEF DESCRIPTION

Reference is now made to the following descriptions taken in conjunction with the accompanying drawings, in which:

FIG. 5 illustrates a cut-away side view of an EEC from FIG. 4;

Figure 6:
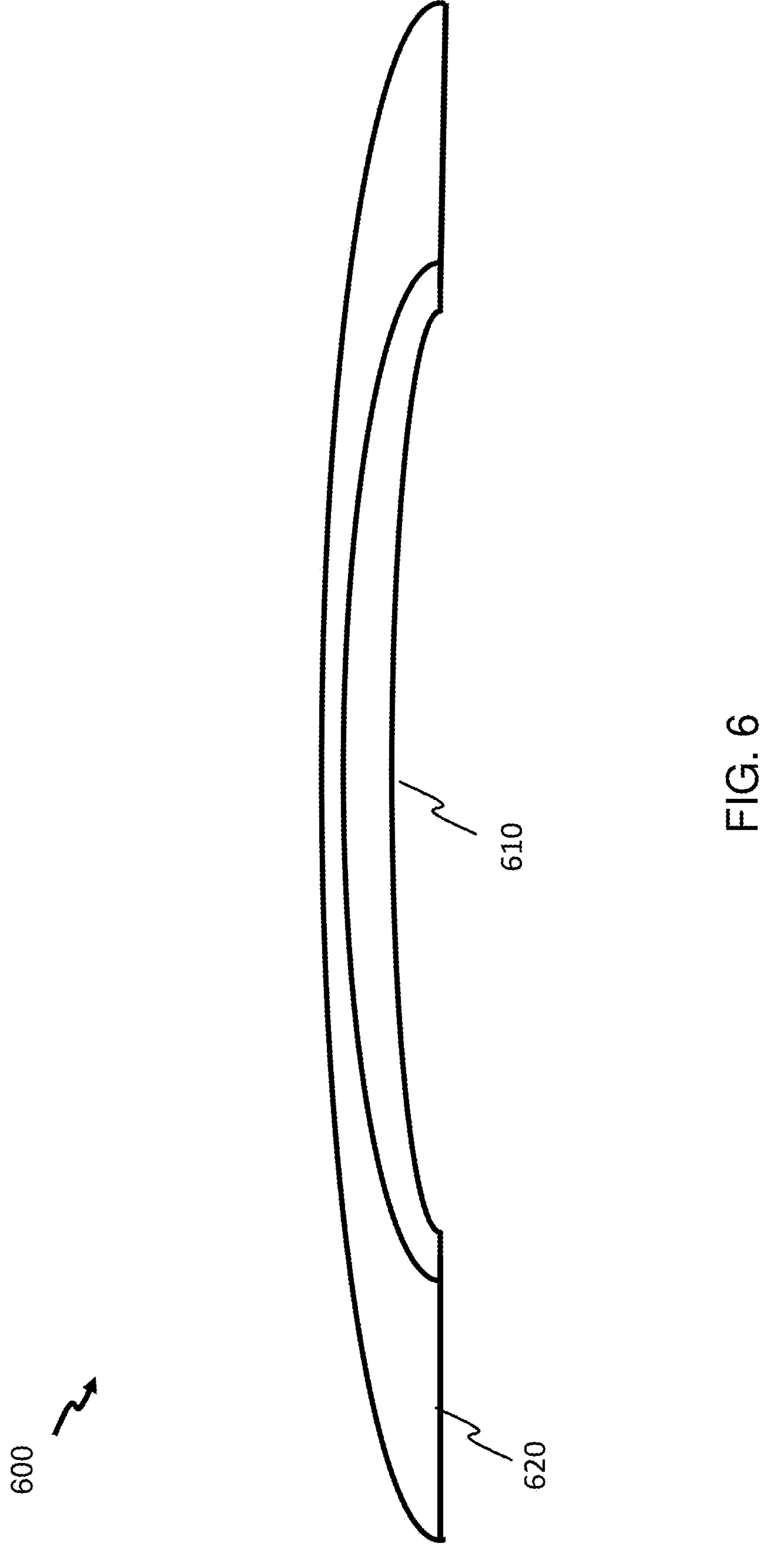
Figure 7:
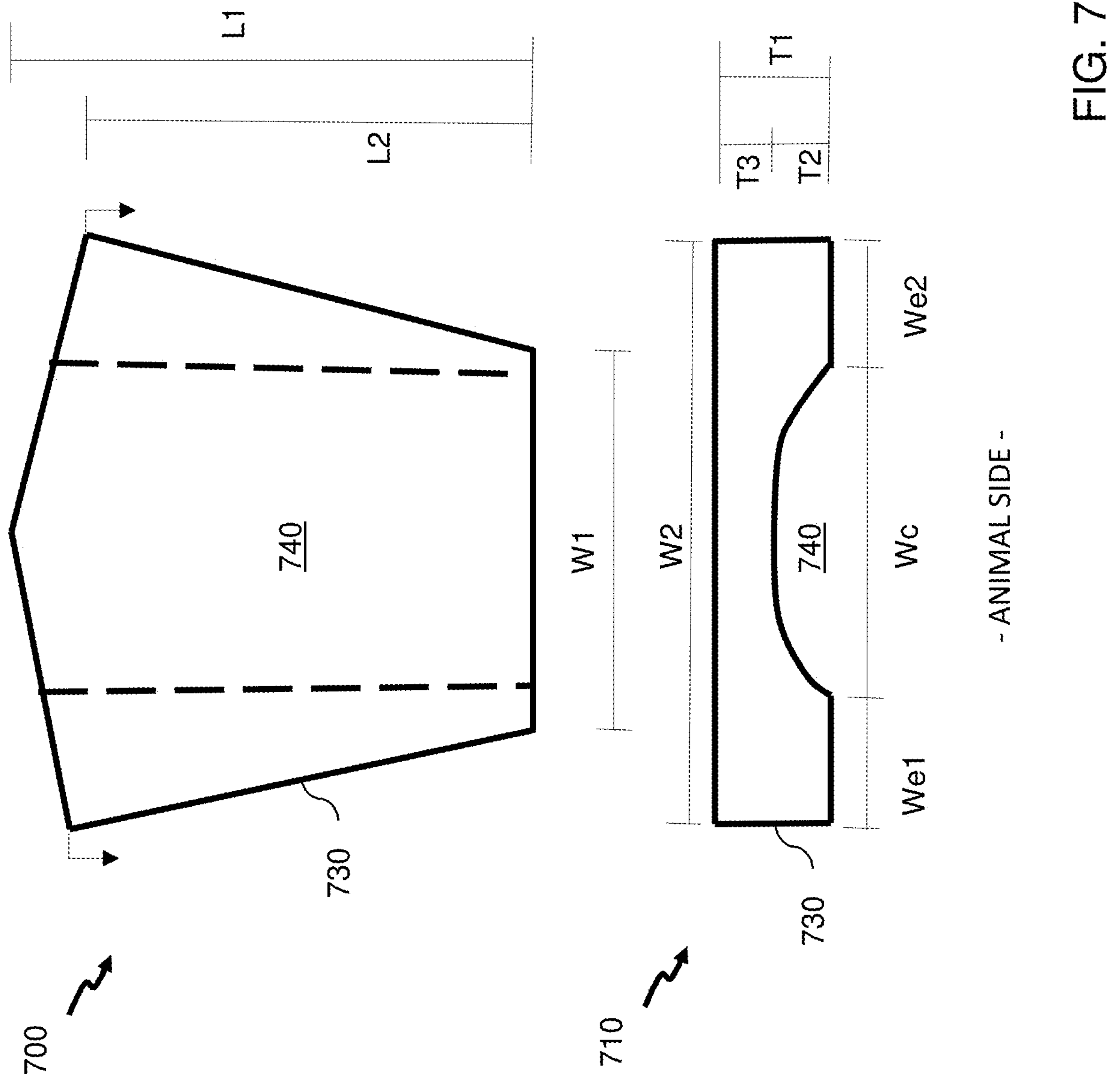
Figure 8:

FIG. 6 provides an example of a cross-section view of an EEC that shows a concave shape of a layer of moldable material and a layer of a pliable material;

FIG. 7 illustrates an example of a moldable material that includes a concave portion constructed according to the principles of the disclosure; and FIG. 8 illustrates an example of a sound protection cap constructed according to the principles of the disclosure being worn by a dog.

DETAILED DESCRIPTION

There are multiple types of products available to protect the hearing of humans. These products, however, are not designed for dogs but instead are made to fit the ears and/or heads of humans. As such, a human-based design, even one designed for children, would not necessarily fit properly on a dog to effectively protect the hearing of the dog. A hearing protection device that is designed based on the anatomy of a dog and other non-human mammals would be beneficial.

The disclosure provides a sound protection cap for animals, such as a dog or another non-human mammal. The disclosed sound protection cap is constructed of formable material and adjustable straps to comfortably fit over the ears and on the head of an animal. The formable material can be soft acoustical material. The sound protection cap can come in different sizes to also insure a good fit regardless the ear type or head shape of the animal. The multiple adjustments and formable material allows the sound protection cap to conform around the ears/head of the animal and stay in place. As such, the sound protection cap can be positioned on an animal to provide hearing protection throughout exposure to loud sounds. This differs from many hearing protection devices for animals that often do not stay in place once initially positioned. Additionally, since the disclosed sound protection cap is made of a soft material and fits snugly on the animal, the animal is less likely to attempt to remove the sound protection cap. The sound protection cap can be worn, for example, while sleeping or during activities such as work, service, recreation, etc. Hunting, airplane travel, concerts, fireworks, and thunder, are just some non-limiting examples of noise that the disclosed sound protection cap can protect against and provide comfort for the animal. With the disclosed protective device, people can take their pets with them for various activities and provide reliable and operable hearing protection for their pets.

Regardless the ear type, the sound protection cap is configured, i.e. designed and constructed, for the anatomy of an animal to protect the animal from hearing loss. For example, the animal can be a dog. Unlike humans, the ear canal openings of dogs align with the back of the skull (i.e., head). Additionally, there are over 300 different breeds of dogs and each has a slightly different shaped head and have a variety of different ear types, including erect ears, drop ears, bat ears, rose ears, butterfly ears, etc. Advantageously, the disclosed sound protection cap includes sound attenuating materials that can wrap around the ear area and behind the head of dogs (and other animals) and adjusted to conform to those areas for sound protection. The sound protection cap includes an external ear cover (EEC) and an adjustable attachment system (AAS) coupled thereto that allows multiple adjustments to wrap around the different types of ears and the back of the head of various types of animals, such as dogs, to remain in place and eliminate (or at least reduce) sound gaps. The EEC includes at least one sound reduction layer that provides sound protection. In some examples, more than one sound reduction layer can be used and the multiple sound reduction layers can include more than one type of material.

The sound reduction layer is constructed of a moldable material that can be, for example, viscoelastic polyurethane foam or low-resilience polyurethane foam (LRPu). In addition to the sound reduction layer, the EEC can include at least one other layer, which can also have sound reduction properties. The other layer can be a layer of a pliable material, such as a molded medium foam (MMF). Other types of similar materials can also be used for the moldable and pliable materials. For example, the pliable material can be a fabric that includes fibers that are natural, synthetic, or a combination thereof.

The moldable material can have a noise reduction rating (NRR) of at least 20 decibels. For example, the moldable material can have a NRR in the range of 20 to 25 decibels. The moldable material can have a NRR less than 20 decibels and moldable materials with different NRR levels can be used interchangeably when the moldable material layer is removably coupled. The moldable material and the pliable material can cooperate to provide a cumulative level of NRR. For example, the pliable material can be neoprene or another type of synthetic rubber that can also contribute to sound protection for the animal.

Figure 1A:
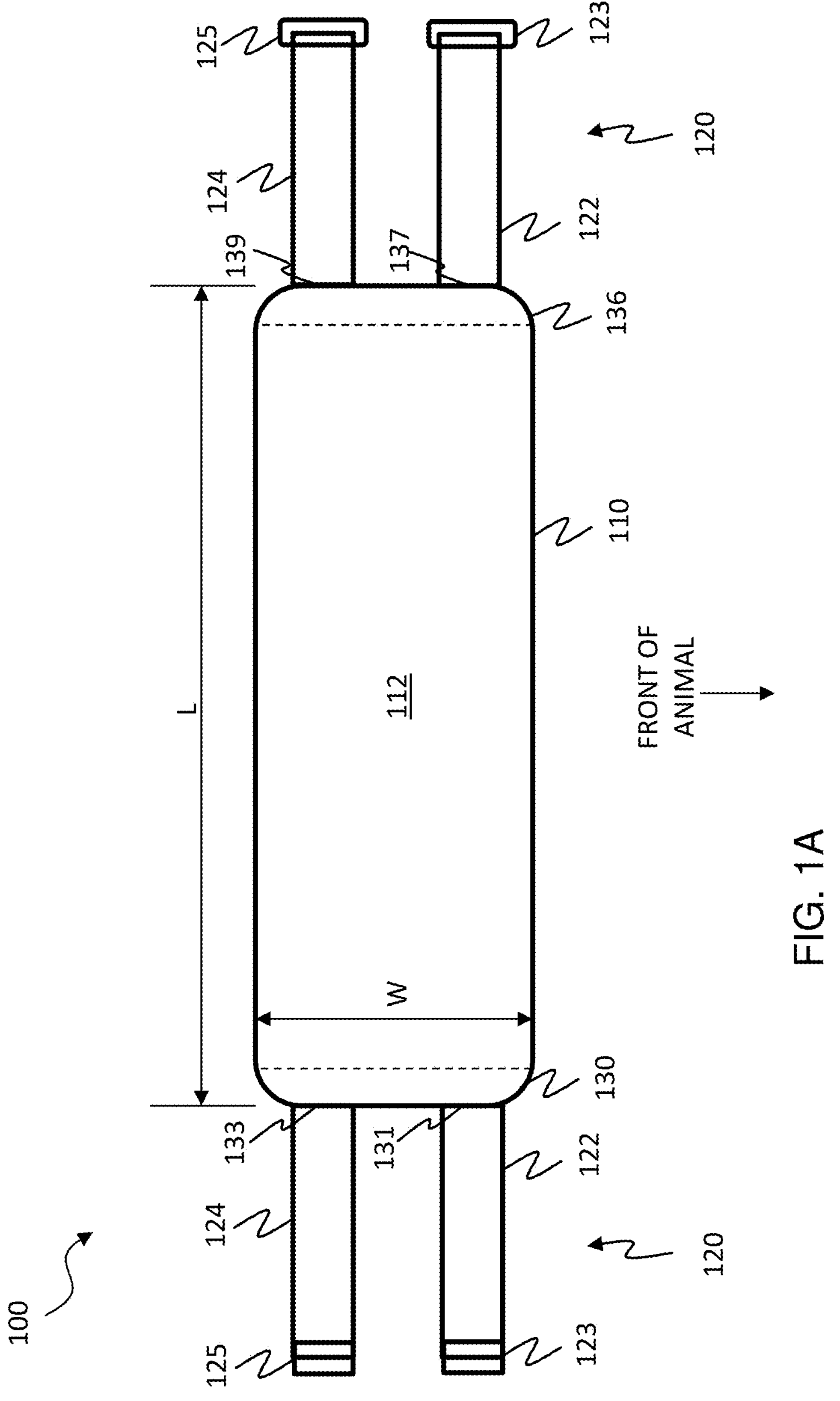
FIG. 1A illustrates a diagram of an example of a sound protection cap for an animal constructed according to the principles of the disclosure.

FIG. 1A illustrates a diagram of an example of a sound protection cap 100 for an animal constructed according to the principles of the disclosure. The sound protection cap 100 includes an EEC 110 and an AAS 120. The EEC 110 has a shape of a rectangle with rounded corners, a width (W) that corresponds to the ear size of the animal, and a length (L) that corresponds to the width of the animal's head. One or more of the shape, width, or length can vary to correspond to the size of the animal or for a particular animal. For example, the EEC 110 can have a width and height for small, medium, large, and/or extra-large dogs, wherein small dogs are between 2 to 23 pounds, medium dogs are between 24 to 58 pounds, large dogs are between 59 to 99 pounds, and extra-large dogs are 100 or more pounds. The width of the EEC 110 can be in the range of, for example, two to three inches for small dogs, three to four inches for medium dogs, four to five inches for large dogs, and five to six inches for extra-large dogs. For other animals, such as horses, the dimensions of the EEC can be even greater, such as a width of more than six inches. The number of different sizes of the sound protection cap 100 can vary and ranges for one or more of the dimensions of the different sizes can overlap.

Figure 3:
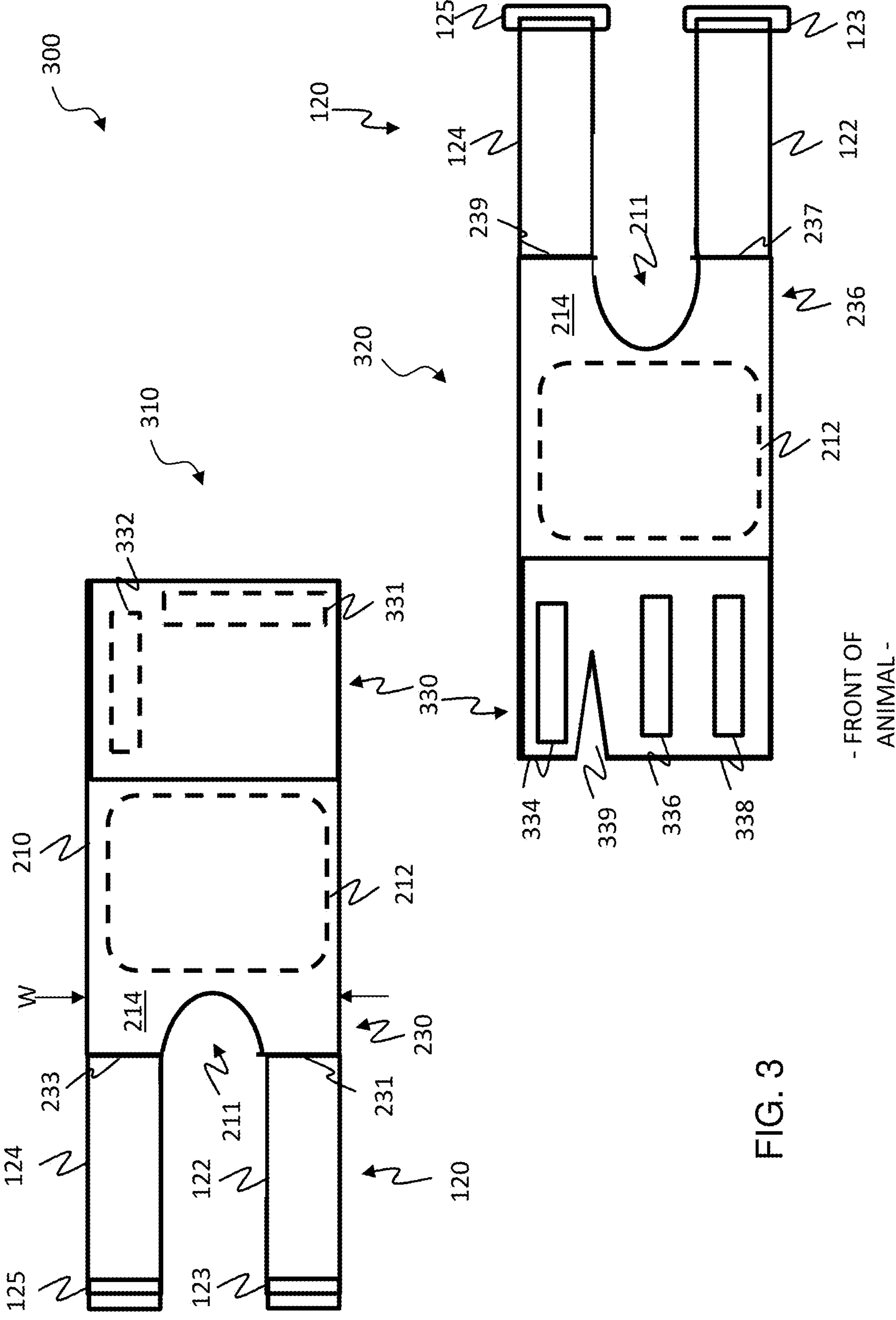
FIG. 3 illustrates a diagram of an example of a sound protection cap having two removably coupled EECs constructed according to the principles of the disclosure.
Figure 4:
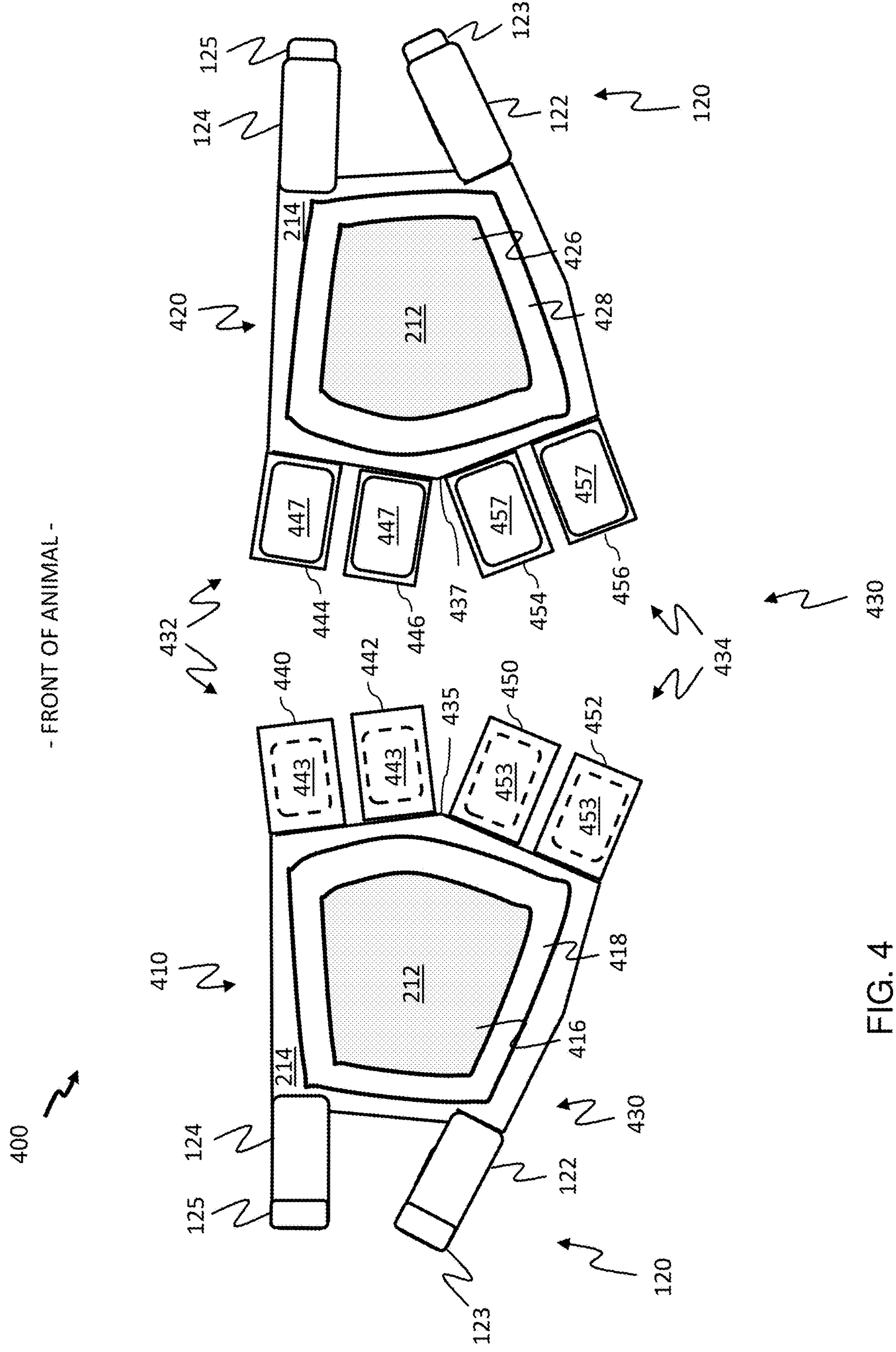
FIG. 4 illustrates a diagram of another example of a sound protection cap having two removably coupled EECs constructed according to the principles of the disclosure.

The EEC 110 is a single piece. In some examples, the EEC 110 can be in at least two pieces that are removably coupled together. The two pieces can be removably coupled together via a mounting adjustor, such as illustrated in FIGS. 3 and 4. A mounting adjustor can be located between the two separate pieces of the EEC to allow adjustments for fitting.

Figure 2:
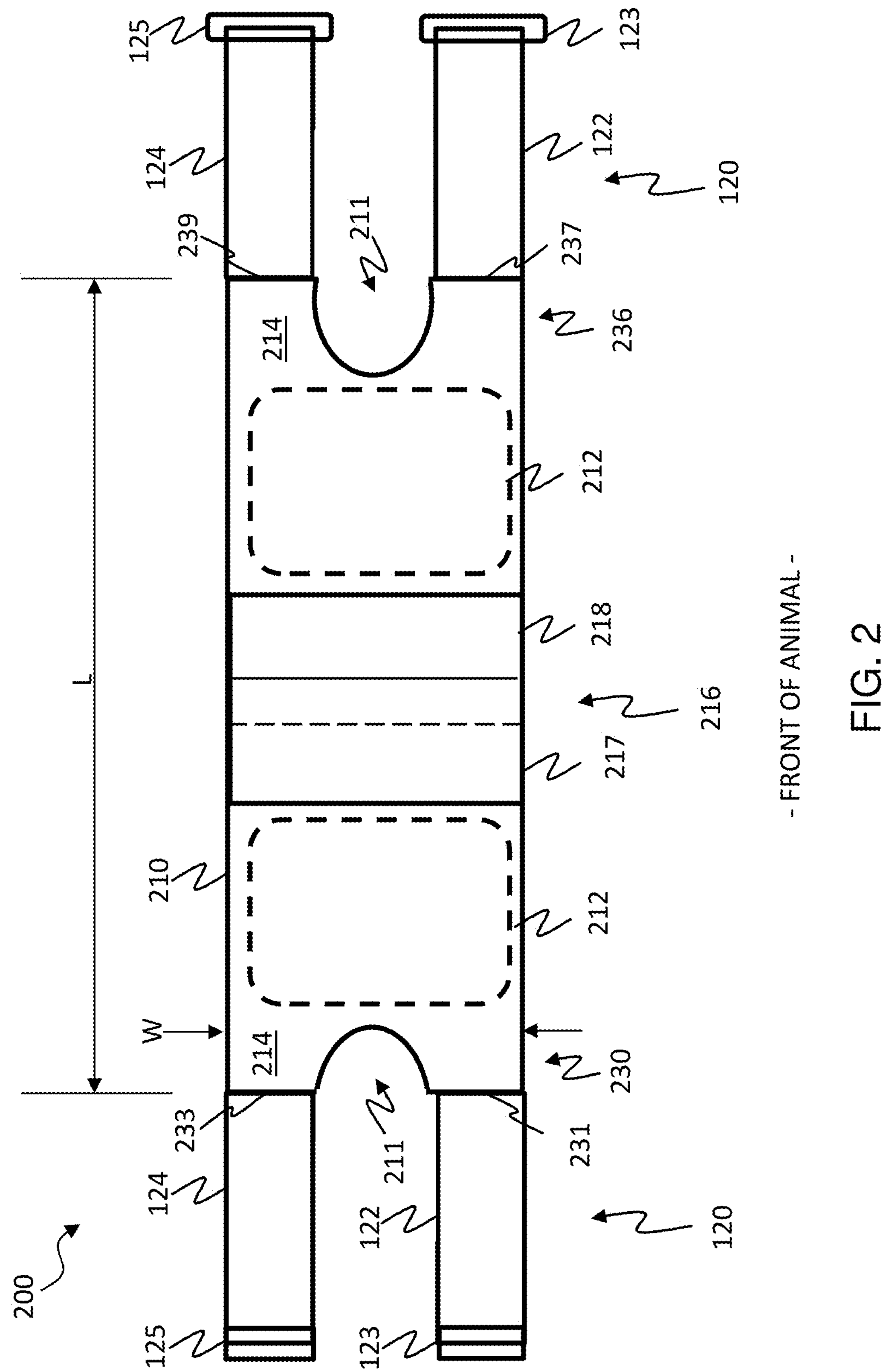
FIG. 2 illustrates a diagram of another example of a sound protection cap for an animal constructed according to the principles of the disclosure.

The EEC 110 fits over the ears of an animal and includes a moldable material that conforms to the ears. The EEC 110 can also conform to the head, such as the back of the head, of the animal. As illustrated in FIG. 2, a sound protection cap can be a single piece that has separate sections of moldable material for each animal ear. In addition to a layer of the moldable material, the EEC 110 can also include a layer of another type of material that is pliable. The two layers can be permanently affixed together via, for example, an adhesive. The two layers can also be permanently affixed together by being sewed together or via another type of mechanical connection. Element 112 represents an area of the EEC 110 that includes both the moldable material and the pliable material. The moldable material layer typically is considered the layer that provides the greatest sound reduction or protection. However, as noted above the pliable layer can also contribute to sound protection. As such, the moldable material can be a first sound reduction layer and the pliable material can be a second sound reduction layer. The pliable material can extend past the edges of the moldable material (denoted by dashed lines in FIG. 1A) in at least one direction to create attachment areas 130 and 136. In some examples, such as in FIGS. 2, 3, and 4, at least portions of the layer of pliable material wholly encompasses the moldable material, i.e., extends past the moldable material in every direction.

In the attachment areas 130, 136, the AAS 120 can be attached to the EEC 110. Tightening the EEC 110 around the neck and ears of the animal via the attachment areas 130, 136, contributes to conforming the moldable material of the EEC 110 to the ears and head of the animal. The pliable material layer can have a greater mechanical strength along a tightening axis, for example, in-line with the straps 122, 124, than the moldable material layer to assist in the tightening and conforming of the moldable material. The moldable material layer, the pliable material layer, or both can have a concave shape that further contributes to the EEC 110 conforming around the head and ears of the animal. FIG. 6 and FIG. 7 provide examples of a side view of an EEC and a moldable material that show a concave shape. The size of the attachment areas 130, 136, can vary and correspond to the various sizes of the sound protection cap 100. The thickness of the moldable material and pliable material of an EEC can also correspond to the different sizes of the sound protection cap 100. The thickness of each layer of material can also vary in an EEC. For example, the EEC 110 can have the shape of an airplane wing and the moldable material and/or pliable material can be thicker in one layer area versus another layer area. In some examples, a thickness of the moldable material can be in the range of ¾" to 1¼" in at least one area. The pliable material can have a thickness, for example, of ¼" to ¾".

The AAC 120 is configured to secure the EEC 110 over the ears of the animal. The AAC 120 includes two straps 122, 124. The straps 122, 124, are partitioned into two sections that are connected together via connectors 123, 125, to form adjustable straps 122, 124. The connectors 123, 125, can be of various types, such as a type of buckle, a snap, or a hook and loop fastener. The connectors 123, 125, can also be different types of connectors. For example, connector 123 can be a snap connector and connector 125 can be a hook and loop fastener. The connectors 123, 125, can allow for changing the length of the adjustable straps 122, 124, to provide adjustments to secure the sound protection cap 100 over the ears of the animal. For example, the connectors 123, 125, can be adjustable side release buckles, slip lock buckles, or another type of connector that allows adjustments of the straps 122, 124, for fitting around the head and ears of the animal. The strap 122 is connected to the EEC 110 at connection points 131 and 137, and the strap 124 is connected to the EEC 110 at connection points 133 and 139.

The strap 122 can be referred to as an ear strap and can be typically positioned around the head, such as the forehead area of the animal in front of the ears of the animal. The strap 124 can be referred to as a neck strap and can be typically positioned around the neck of the animal behind the ears of the animal. The straps 122, 124, can be independently adjusted to ensure proper placement of the EEC 110 over the ears for noise protection and to secure the sound protection cap 100 in place around the head of the animal.

Figure 1B:
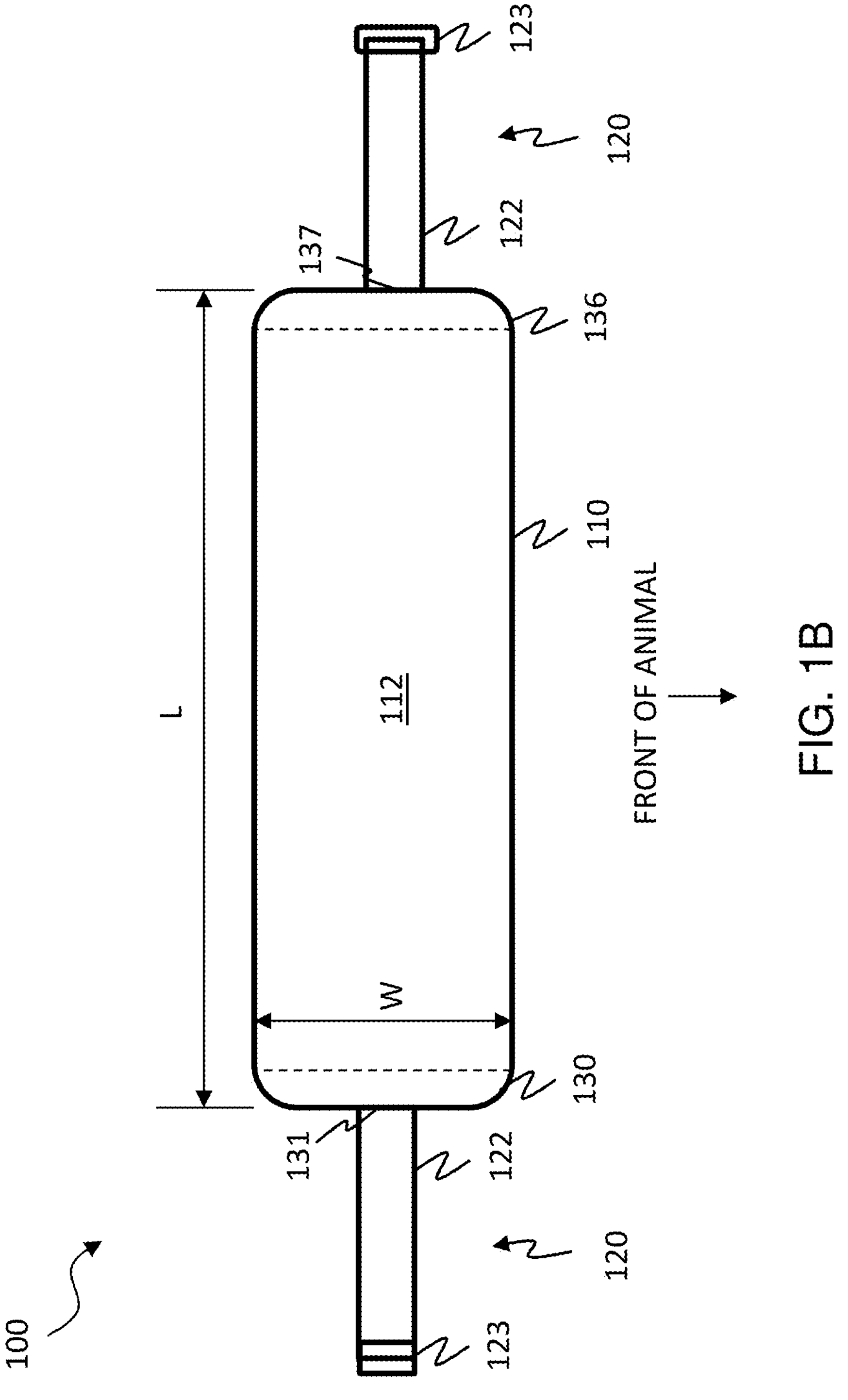
FIG. 1B illustrates a diagram of an example of a sound protection cap for an animal that has a single adjustable strap.

In other examples, the AAS 120 can include a single strap. FIG. 1B provides an example of a single strap using strap 122 as an example. The AAS 120 with a single strap can also be used with the illustrated examples of FIGS. 2-3.

FIG. 2 illustrates a diagram of another example of a sound protection cap 200 for an animal constructed according to the principles of the disclosure. The sound protection cap 200 includes an EEC 210 and an AAS, which can be constructed as the AAS of FIG. 1A and as such is referred to as AAS 120. Like the EEC 110, the EEC 210 is also configured to fit over the ears and around the head of an animal for noise protection. Unlike the EEC 110, the EEC 210 includes indentations 211 along each width end. The indentations 211 assist with adjustments for a secure fit around the ears of each individual animal by, for example, allowing movement of the straps 122, 124, of the AAS 120 around the ears. The straps 122, 124, are connected to the EEC 210 at connection points 231 and 237, and at connection points 233 and 239. One or more of the connection points 231, 233, 237, and 239, can be angled to improve the fit around the animal's ears and head. The straps 122, 124, can be connected to the connection points 231, 233, 237, and 239, via a mechanical connection that is removably or permanently affixed. For example, the straps can be sewed to the connection points 231, 233, 237, 239. In some examples, the straps 122, 124, can be removably connected to one or more of the connection points 231, 233, 237, and 239 or sides to allow adjustments at the connection points. For example, hook and loop fasteners or snaps can be used for adjustments. Similar types of connections can also be used for the other sound protection caps disclosed herein, such as in FIGS. 1A, 1B, 3 and 4.

As with the EEC 110, the EEC 210 has a width (W) that corresponds to the ear size of the animal, and a length (L) that corresponds to the width of the animal's head. Additionally, one or more of the shape, width, or length of the EEC 210 can vary to correspond to the size of the animal or for a particular animal.

The EEC 210 is a single piece that includes a layer of moldable material 212 and a pliable material 214. The moldable material 212 is in two separate sections in this example that each fit over a different ear of the animal. The EEC 210 also includes a mounting adjustor 216 located between the two separate layers of moldable material 212 to allow adjustments for fitting the animals. The mounting adjustor 216 can include multiple hook and loop fasteners that provide individual adjustments for the ears and the head of the animal. The mounting adjustor 216 includes a first piece 217 that overlaps a second piece 218. The hooks or the loops can be on either of the first piece 217 or the second piece 218. The mounting adjustor 216 can include a non-slip portion or a non-slip side, which aids in keeping the sound protection cap 200 in the proper position to provide sound protection for the animal. For example, the animal side of the mounting adjustor 216 can include a non-slip or slip-resistant material, such as a synthetic rubber (e.g., neoprene), or portions of material that aid the sound protection cap 200 from moving. FIGS. 3 and 4 provide examples of a mounting adjustor that is partitioned onto two corresponding EECs and that includes both neck and ear adjustments.

The moldable material 212 and the pliable material 214 can be permanently affixed together via a chemical or mechanical connection. In some examples, the moldable material 212 can be removably attached to the pliable material 214, such as via snaps, buttons, etc. The pliable material 214 can also include pouches or pockets wherein the moldable material can fit. By being removably attached, the moldable material 212 can be replaced if needed. Additionally, materials with different levels of noise abatement can be interchanged depending on the activity the animal will be involved in or exposed to. The pliable material 214 can also form a pocket for the moldable material 212 wherein the pliable material 214 is permanently closed around the moldable material 212 by, for example, being sewed or stapled. As illustrated in FIGS. 4 and 5, the moldable material 212 can be contained within a pocket by a barrier and a border.

The pliable material 214 extends past the end of the moldable material 212 to create attachment areas 230 and 236. In the attachment areas 230, 236, the AAS 120 can be attached to the EEC 210. Tightening the EEC 110 around the neck and ears of the animal via the attachment areas 230, 236, contributes to conforming the moldable material 212 of the EEC 210 to the ears and also the head of the animal. The moldable material layer, the pliable material layer, or both can have a concave shape that further contributes to the conforming of the EEC 210 as shown in FIGS. 6 and 7. The size of the attachment areas 230, 236, can vary and correspond to the various sizes of the sound protection cap 200. As with FIG. 1A, the moldable material can be a LRPu and the pliable material can be an MMF. The pliable material can also be a synthetic rubber.

FIG. 3 illustrates a diagram of an example of a sound protection cap 300 having two removably coupled EECs 310, 320. The two EECs 310, 320, are removably coupled together via a mounting adjustor 330. The same element numbers are used in FIG. 3 for similar components used in FIGS. 1A, 1B, and/or 2.

The mounting adjustor 330 includes a neck adjustor and an ear adjustor. A portion of the neck adjustor and a portion of the ear adjustor are on EEC 310 and EEC 320. The ear adjustor includes elements 331 and elements 336, and 338. Element 331 can be a loop section and elements 336 and 338 can be a hook section that cooperate for adjustable connections. Similarly, element 332 can be a loop section and element 334 can be a hook section that cooperate for adjustable connections corresponding to the neck of the animal around the ears (the neck adjustor). The hook and loop combinations can be low profile. The loop portions of the adjustors can be located on the top EEC to reduce snagging of the animal. As such, EEC 310 can be considered the top EEC. The mounting adjustor 330 also includes a recess or slit 339 that cooperates with the neck and ear adjustors for conforming the EEC 310 and the EEC 320 to the animals' head and securely over the animal's ears. Instead of a hook and loop, another type of adjustable connection system can be used. As noted above with respect to the mounting adjustor 216 of FIG. 2, the mounting adjustor 330 can also include a non-slip side or portion to resist movement of the sound protection cap 300 once positioned. For example, neoprene can be used to reduce movement and provide a soft layer of material against the animal. The mounting adjustors 216, 330, or a portion thereof can be constructed of a different material than the moldable or pliable material, or can include one or more of the moldable or pliable material.

FIG. 4 illustrates a diagram of another example of a sound protection cap 400 constructed according to the principles of the disclosure. The same element numbers are used in FIG. 4 for similar components used in FIG. 1A, 1B, 2, or 3. As with the sound protection cap 300, the sound protection cap 400 has two removably coupled EECs 410, 420. The EECs 410, 420, are removably coupled together via a mounting adjustor 430.

The mounting adjustor 430 includes an ear adjustor 432 and a neck adjustor 434, wherein a portion of the ear adjustor 432 and a portion of the neck adjustor 434 are on EEC 410 and EEC 420. The ear adjustor 432 and the neck adjustor 434 include corresponding tabs that are positioned on opposite sides of apex 435 on EEC 410 and apex 437 on EEC 420 that allow individual adjustments for wrapping the sound protection cap 400 over the ears and around the back of the head of the animal for effective sound protection. Each of the tabs can include a corresponding portion of an adjustable connection system that assists in conforming the EEC 410 and the EEC 420 to the animals' head and securely over the animal's ears. A hook and loop system as discussed herein will be used as an example but another type of adjustable connection system can be used. The ear adjustor 432 includes tabs 440, 442, attached to EEC 410 and tabs 444, 446, attached to EEC 420. Each of the tabs 440 and 442 include a hook section 443 and each of the tabs 444, 446, include a corresponding loop section 447 that cooperate for adjustable connections. Similarly, the neck adjustor 434 includes tabs 450, 452, attached to EEC 410 and tabs 454, 456, attached to EEC 420. Each of the tabs 450 and 452 include a hook section 453 and each of the tabs 454, 456, include a corresponding loop section 457 that cooperate for adjustable connections. The hook and loop combinations can be low profile. The loop portions of the adjustors can be located on the top EEC when positioned on the animal to reduce snagging of the animal. As such, EEC 420 can be considered the top EEC. As noted above with respect to the mounting adjustor 330 of FIG. 2, the mounting adjustor 430 can also include a non-slip side or portion to resist movement of the sound protection cap 400 once positioned. For example, neoprene can be on the animal side of tabs 440, 442, 450, 452, which is on the opposite side of the hook sections 443, 453.

In addition to the moldable material 212 and the pliable material 214, the EECs 410 and 420 include a barrier 416, 426, that protects and contains the moldable material 212 and allows stretching of the moldable material 212 over the ears of the animal. The barriers 416, 426, can be constructed of spandex or another similar sturdy and stretchable material. The moldable material 212 is located behind the barriers 416, 426. Borders 418, 428, are used to define the location of the moldable material 212 and secure the barriers 416, 426, to the pliable material 214 of the EECs 410, 420. The borders 416, 426, can be constructed of a synthetic rubber, such as neoprene. The mounting adjustors 430, or a portion thereof can be constructed of a different material than the moldable or pliable material, or can include one or more of the moldable or pliable material.

FIG. 5 illustrates a side view 500 of EEC 420 from FIG. 4. The side view 500 is a cut-away view that illustrates the configuration of the moldable material 212 contained within an outer layer of the pliable material 214 and the barrier 426. In this example, the moldable material 212 is located within a pocket. As discussed above regarding FIG. 2, the moldable material 212 can be permanently positioned within the pocket or removable with respect to the pocket. The border 428 supports the barrier 426 and connects the barrier 426 to the pliable material 214. The border 428 can be constructed of a soft material to provide a comfortable interface between the EEC 420 and the animal. The material of the border 428 can also have a rubber-like property to reduce sliding. Both material properties can individually and collectively contribute to lesson the impulse of the animal to attempt to remove the EEC 420. As noted above, the border 428 can be constructed of neoprene. In addition to the sound reduction layer of the moldable material 212, another sound reduction layer can be positioned between the moldable material 212 and the outer pliable material 214. For example, a silicon layer can be placed between moldable material 212 and the outer covering of the pliable material 214.

The moldable material 212 in FIG. 5 is in the shape of a hemisphere. The moldable material 212 can have a concave shape or concave portion. FIGS. 6 and 7 provide examples of a moldable material with at least a concave portion.

FIG. 6 provides an example of a cross-section view of an EEC 600 that shows a concave shape of a layer of moldable material 610 and a layer of a pliable material 620. The cross-section view of FIG. 6 can be along the width of an EEC, such as the width shown in FIGS. 1-3. The cross-section view can also represent a length or a portion of a length of an EEC. For example, the moldable material 212 in FIG. 3 can be concave along the width and the length to form a cup-shape. As illustrated, the pliable material 620 can also have a concave shape along the width, the length, or both of the EEC 600.

In some examples, neither the moldable material nor the pliable material of an EEC may have a concave shape. In some examples, the layer of moldable material and the layer of pliable material of an EEC can have a shape of an airplane wing. For example, the cross section of the layer of moldable material and/or the layer of pliable material can correspond to an airfoil, such as a symmetrical or cambered airfoil. The thinner portion of the airfoil can be located closest to the AAS 120. The thick portion of the airfoil portion for the moldable material layer can have a thickness in the range of, for example, 1" to 1½"; in some examples the thick portion can be 1¼". The length and width of the moldable material layer can be in the range of, for example, 3" to 5"; in some examples the moldable material layer can be 4" by 4".

FIG. 7 illustrates another example of a moldable material that includes a concave portion. A top view 700 and a section cut view 710 of the moldable material 730 are illustrated. The moldable material 730 is a polyhedron with a concave portion 740 located along the length of moldable material 730 in the center or proximate the center thereof. As seen in the top view 710, the moldable material 730 has a pentagon face. The concave portion 740 can be seen in the side view 710 and corresponds to the dashed lines in the top view 700. With the concave portion 740, the moldable material 730 can be considered a modified pentagonal prism. Instead of a modified pentagonal prism, the moldable material 730 can be another type of polyhedron. Regardless the type of polyhedron, the moldable material 730 may or may not include a concave portion.

The dimensions of the moldable material can vary depending on, for example, the size of EEC and the animal or animal type for which it is configured. In FIG. 7, for example, the length L1 can be in the range of 3" to 4" and the length L1 can be in the range of 3.5" to 4.5". Examples of the width ranges are 2.5" to 3" for W1 and 4" to 5" for W2.

The section cut view 710 illustrates the thickness T1 of the moldable material 730 and dimensions of the concave portion 740. For example, T1 can be 0.75" to 2.5", T2 can be 0.25" to 1" and T3 can be 0.5" to 1.5". The width of the concave portion 740 $W_c$ can be from 2" to 3". The distance between the concave portion 740 and the edges, $W_{e1}$ and $W_{e2}$, will vary depending on the other dimensions of the moldable material 730 and the concave portion 740. In one example, $W_{e1}$ and $W_{e2}$ are both 1", T1 is an 1", T2 is 0.25", T3 is 0.75", W1, is 2.75", W2 is 4.5", L1 is 4", and L2 is 3.5".

FIG. 8 illustrates an example of a sound protection cap 800 constructed according to the principles of the disclosure being worn by a dog. For example, the sound protection cap can be the sound protection cap as disclosed in FIGS. 3 and 4.

Those skilled in the art to which this application relates will appreciate that other and further additions, deletions, substitutions and modifications may be made to the described embodiments.

Each aspect of the Summary can include one or more of the additional elements of the below dependent claims in combination.

What is claimed is:

1. A sound protection cap for an animal having a neck strap and an ear strap, comprising:
- an external ear cover (EEC); and
- a mounting adjuster having a neck adjuster and an ear adjuster positioned on opposite sides of an apex of the EEC that are adjustable for conforming the EEC around the head and ears of the animal, wherein the neck adjuster is adjustable for positioning the neck strap around the neck and behind the ears of the animal and the ear adjuster is adjustable for positioning the ear strap around the head and in front of the ears.

2. The sound protection cap as recited in claim 1, wherein the neck adjuster and the ear adjuster each include at least one tab attached to the EEC.

3. The sound protection cap as recited in claim 1, wherein the neck adjuster and the ear adjuster each have two sides and include at least a portion of a non-slip surface on one of the two sides.

4. The sound protection cap as recited in claim 1, wherein the EEC includes a first EEC and a second EEC and the mounting adjuster is positioned between the first and the second EEC.

5. The sound protection cap as recited in claim 4, wherein the first EEC is removably coupled to the second EEC by the mounting adjuster.

6. The sound protection cap as recited in claim 5, wherein the first EEC has a shape of a pentagonal prism with a concave portion positionable to conform around the head and a first one of the ears of the animal.

7. The sound protection cap as recited in claim 6, wherein the second EEC has a shape of a pentagonal prism with a concave portion positionable to conform around the head and a second one of the ears of the animal.

8. The sound protection cap as recited in claim 1, wherein the mounting adjuster includes multiple hook and loop fasteners.

9. The sound protection cap as recited in claim 1, wherein the mounting adjuster is configured to cooperate with the neck strap and the ear strap to conform the sound protection cap to the head of the animal and secure the sound protection cap against the ears of the animal.

10. The sound protection cap as recited in claim 1, wherein the EEC includes a sound reduction layer that is a low-resilience polyurethane foam (LRPu) layer.

11. The sound protection cap as recited in claim 10, wherein the EEC further comprises a second layer that wholly encompasses the sound reduction layer.

12. The sound protection cap as recited in claim 11, wherein the second layer is a layer of a pliable material.

13. The sound protection cap as recited in claim 12, wherein the pliable material is synthetic rubber.

14. The sound protection cap as recited in claim 13, wherein the pliable material is neoprene.

15. The sound protection cap as recited in claim 11, wherein the second layer is a layer of silicon.

16. A sound protection cap for an animal, comprising:
- an adjustable neck strap;
- an adjustable ear strap;
- a first external ear cover (EEC) and a second EEC that each include a sound reduction layer and a layer of pliable material, wherein the adjustable neck strap and the adjustable ear strap are coupled to the first EEC and the second EEC; and
- a mounting adjuster having a neck adjuster and an ear adjuster attached to opposite sides of an apex of the first EEC and an apex of the second EEC, wherein the neck adjuster is adjustable for positioning the adjustable neck strap around the neck and behind the ears of an animal and the ear adjuster is adjustable for positioning the adjustable ear strap around the head and in front of the ears.

17. The sound protection cap as recited in claim 16, wherein the first EEC is removably coupled to the second EEC by the mounting adjuster, the neck adjuster includes at least one tab attached to each of the first EEC and the second EEC, and the ear adjuster includes at least one different tab attached to each of the first EEC and the second EEC.

18. A sound protection cap for an animal, comprising:
- a first external ear cover (EEC) and a second EEC that each include at least one sound reduction layer having a shape of a pentagonal prism with a concave portion,
- a mounting adjuster, removably coupled to the first EEC and the second EEC, wherein the mounting adjuster includes a neck adjuster and an ear adjuster attached to opposite sides of an apex of the first EEC and an apex of the second EEC, wherein the neck adjuster is adjustable for positioning an adjustable neck strap around the neck and behind the ears of the animal and the ear adjuster is adjustable for positioning an adjustable ear strap around the head an in front of the ears.

19. The sound protection cap as recited in claim 18, wherein each of the first EEC and the second EEC include at least one additional sound reduction layer that is a silicon layer.

20. The sound protection cap as recited in claim 18, wherein each of the first EEC and the second EEC include at least one additional sound reduction layer that is a layer of synthetic rubber.

* * * * *